United States Patent
Tomlinson et al.

(10) Patent No.: US 8,901,355 B2
(45) Date of Patent: Dec. 2, 2014

(54) DENDRIMERS AND METHODS FOR THEIR PREPARATION

(75) Inventors: Ian A. Tomlinson, Midland, MI (US); Asghar A. Peera, Buffalo Grove, IL (US)

(73) Assignees: Dow Global Technologies LLC, Midland, MI (US); ANGUS Chemical Company, Midland, MI (US)

(*) Notice: Subject to any disclaimer, the term of this patent is extended or adjusted under 35 U.S.C. 154(b) by 0 days.

(21) Appl. No.: 14/118,620

(22) PCT Filed: May 17, 2012

(86) PCT No.: PCT/US2012/038362
§ 371 (c)(1),
(2), (4) Date: Nov. 19, 2013

(87) PCT Pub. No.: WO2012/173736
PCT Pub. Date: Dec. 20, 2012

(65) Prior Publication Data
US 2014/0107376 A1    Apr. 17, 2014

Related U.S. Application Data

(60) Provisional application No. 61/497,551, filed on Jun. 16, 2011.

(51) Int. Cl.
| | | |
|---|---|---|
| C07C 215/18 | (2006.01) |
| C07C 213/00 | (2006.01) |
| C07C 229/22 | (2006.01) |
| C07C 227/04 | (2006.01) |
| C07C 229/16 | (2006.01) |
| C08G 65/02 | (2006.01) |
| C08G 65/22 | (2006.01) |
| C08G 83/00 | (2006.01) |

(52) U.S. Cl.
CPC .............. *C07C 229/16* (2013.01); *C08G 65/02* (2013.01); *C08G 65/22* (2013.01); *C08G 83/003* (2013.01); *C07C 213/00* (2013.01); *C07C 215/18* (2013.01); *C07C 227/04* (2013.01)
USPC ............ 564/507; 564/475; 564/512; 562/564

(58) Field of Classification Search
None
See application file for complete search history.

(56) References Cited

U.S. PATENT DOCUMENTS

| | | |
|---|---|---|
| 5,760,142 A | 6/1998 | Klee |
| 2007/0073004 A1 | 3/2007 | Tomalia et al. |
| 2007/0244296 A1 | 10/2007 | Tomalia et al. |
| 2007/0298006 A1 | 12/2007 | Tomalia et al. |
| 2010/0086482 A1 | 4/2010 | Tomalia et al. |
| 2010/0178699 A1* | 7/2010 | Gao et al. ................ 435/375 |
| 2011/0146536 A1* | 6/2011 | Tomlinson et al. ...... 106/287.22 |

* cited by examiner

*Primary Examiner* — Brian J Davis
(74) *Attorney, Agent, or Firm* — Raef M. Shaltout

(57) ABSTRACT

Provided are new dendrimers and processes for making them. The dendrimers are derived from a nitroalkyloxirane compound of formula (III): wherein $R^1$, $R^2$, and $R^3$ are as described herein.

(III)

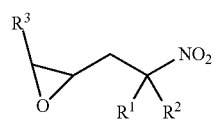

10 Claims, No Drawings

DENDRIMERS AND METHODS FOR THEIR PREPARATION

CROSS-REFERENCE TO RELATED APPLICATIONS

This application is a 35 USC §371 national phase filing of PCT/US2012/0358362 filed May 17, 2012, which claims priority from provisional application Ser. No. 61/497,551, filed Jun. 16, 2011, which is incorporated herein by reference in its entirety.

BACKGROUND

This invention relates generally to starburst dendrimers and their preparation from epoxy-functionalized nitroalkanes.

Starburst dendrimers have been known for more than 25 years and find applications in drug delivery, diagnostics, transfection agents, as catalyst supports and more common applications such as viscosifiers. Dendrimers are generally prepared by sequential reactions which incorporate a branching group. Typical branching groups include amine groups and polyols such as pentaerythritol. Typical reactions used to produce the branches are Michael addition reactions of acrylate esters to amines, followed by amidation reactions e.g. PAMAM dendrimers, or ring opening of (poly)epoxides.

The challenge of current dendrimer syntheses is that reaction steps often require the use of a large excess of one of the reagents, or requires the synthesis of multiple monomers, often with elaborate protection group strategies in order to generate the desired monomers. Even when these elaborate monomers are prepared, changing the chemistry to expand the generations is frequently required because the use of a large excess of a complex multifunctional monomer is simply uneconomical.

The problem addressed by this invention is the provision of new dendrimers and processes for making them that overcome one or more shortcomings of the previously known systems.

STATEMENT OF INVENTION

We have now found that a nitroalkyloxirane monomer of a specific structure as described below provides several benefits when used for the preparation of dendrimers. Advantageously, the monomer may be synthesized easily, does not require a significant excess of reagents at each step of the dendrimer synthesis, and is atom economical. In addition, the monomer may be used to prepare multifunctional dendrimers having well defined structures and which contain functional groups in their interior that may be used for complexation with small molecules (for example pharmaceuticals for applications of drug delivery) or metals for catalysis. Moreover, the monomer does not require elaborate protection and deprotection techniques in order to provide the desired dendrimers. The monomer, therefore, is a versatile and efficient synthon for making macromolecules.

In one aspect, therefore, there is provided a dendrimer comprising:

a core comprising 2 or more terminal residues and derived from a polyvalent organic molecule;

from 1 to 8 generations emanating radially from the core, the 1 to 8 generations comprising:

from 0 to 7 interior generations comprising 2 or more molecular units independently having formula A:

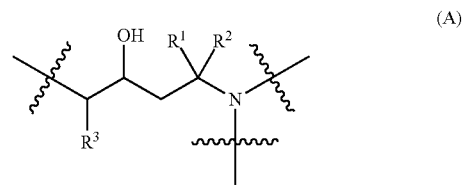

(A)

wherein $R^1$ and $R^2$ are independently H or $C_1$-$C_{10}$ alkyl, or $R^1$ and $R^2$, together with the carbon to which they are attached, form a $C_3$-$C_{12}$ cycloalkyl ring optionally substituted with $C_1$-$C_6$ alkyl, and $R^3$ is H, $C_1$-$C_{10}$ alkyl, or phenyl, and wherein the innermost interior generation is attached to the core through the terminal residues;

an exterior layer attached to the outermost of the interior generations or to the core through the terminal residues if no interior generations are present, the exterior layer comprising 2 or more molecular units independently having formula B:

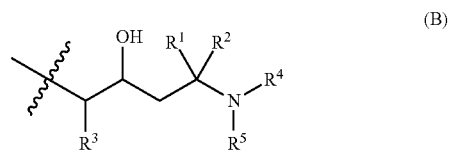

(B)

wherein $R^4$ and $R^5$ are each H, or $R^4$, $R^5$ and the nitrogen to which they are attached form a $NO_2$ group.

In another aspect, there is provided a process for making a dendrimer, the process comprising:

(a) providing a polyvalent organic molecule comprising 2 or more terminal functional groups;

(b) combining a nitroalkyloxirane compound of formula III:

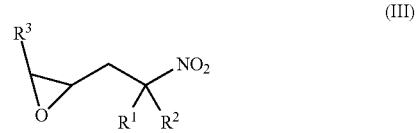

(III)

with the polyvalent organic molecule in sufficient amount such that the nitroalkyloxirane compound reacts with the terminal functional groups of the polyvalent organic molecule to form a nitro compound comprising a core and 2 or more molecular units connected to the core and independently having formula B-1:

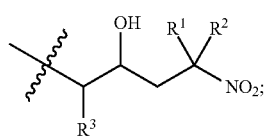

(B-1)

(c) optionally reducing the nitro compound to form an amine compound comprising the core and 2 or more molecular units connected to the core and independently having formula B-2:

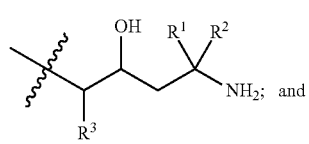

(B-2)

(d) optionally repeating steps (b) and/or (c) from 1 to 7 times, wherein the amine compound instead of the polyvalent organic molecule is reacted with a nitroalkyloxirane compound of formula III, to provide the dendrimer.

DETAILED DESCRIPTION

Unless otherwise indicated, numeric ranges, for instance as in "from 2 to 10," are inclusive of the numbers defining the range (e.g., 2 and 10).

"Alkyl," as used in this specification, encompasses straight and branched chain aliphatic groups having the indicated number of carbon atoms. Preferred alkyl groups include, without limitation, methyl, ethyl, propyl, isopropyl, butyl, isobutyl, sec-butyl, tert-butyl, pentyl, and hexyl. The alkyl group is optionally substituted with 1, 2, or 3, preferably 1 or 2, more preferably 1, substituents independently selected from aryl (preferably phenyl) and $C_3$-$C_{12}$ cycloalkyl. In some embodiments, the alkyl group is not substituted.

The term "cycloalkyl" refers to saturated and partially unsaturated cyclic hydrocarbon groups having the indicated number of ring carbon atoms. Cycloalkyl preferably contains 3 to 8 carbons, and more preferably 3 to 7 carbons. Preferred cycloalkyl groups include, without limitation, cyclopropyl, cyclobutyl, cyclopentyl, cyclopentenyl, cyclohexyl, cyclohexenyl, and cycloheptyl. Unless otherwise indicated, the cycloalkyl group is optionally substituted with 1, 2, or 3, preferably 1 or 2, more preferably 1, substituents selected from: aryl (preferably phenyl) and $C_1$-$C_6$ alkyl. A preferred substituent is $C_1$-$C_6$ alkyl. In some embodiments, the cycloalkyl is not substituted.

An "aryl" group is a C6-C12 aromatic moiety comprising one to three aromatic rings. Preferably, the aryl group is a C6-C10 aryl group. Preferred aryl include, without limitation, phenyl, naphthyl, anthracenyl, and fluorenyl. More preferred are phenyl and naphthyl.

"Heteroaryl" refers to an aromatic ring system containing at least one heteroatom selected from nitrogen, oxygen, and sulfur. The heteroaryl ring may be fused or otherwise attached to one or more heteroaryl rings, aromatic or non-aromatic hydrocarbon rings or heterocycloalkyl rings. Examples of heteroaryl groups include, without limitation, pyridine and furan.

The dendrimers of the invention comprise a core that contains at least 2 terminal residues. The core serves as the nucleus to which the innermost generation of the dendrimer layers are attached, through the terminal residues. The particular structure of the core is not critical to the invention, and a wide variety of materials may be suitably used. By way of non-limiting example, the core may, for instance, be the residue of: an alicyclic or an aliphatic acyclic compound; an aryl compound; a heterocyclic compound containing N, O, and/or S atoms; a heteroaryl compound containing N, O, and/or S atoms; or combinations of such residues, or it may be a functionalized polymer containing a large number (e.g., 10 or more) of terminal residues. In some embodiments, the core is an aliphatic acyclic residue that is a $C_1$-$C_{10}$ alkyl, alternatively $C_2$-$C_8$ alkyl, alternatively $C_3$-$C_6$ alkyl, or alternatively n-hexyl.

The core contains at least 2 terminal residues which, as noted, connect the core to the innermost generation of the dendrimer layers. In some embodiments, the core contains 2 to 6, alternatively 2 to 5, alternatively 2 to 4, alternatively 2 to 3, or alternatively 2 terminal residues. In some embodiments, the terminal residues are amine residues, hydroxyl residues, thiol residues, or combinations of two or more thereof. Amine residues are preferred.

In some embodiments of the invention, when the core is an aliphatic acyclic residue containing 2 amine residues, then the dendrimer comprises at least 2 generations.

The dendrimer comprises from 1 to 8 generations or layers of molecules that emanate radially from the core. If the dendrimer comprises more than one generation, then the generations between the core and the outermost layer are referred to herein as interior generations. Of these, the generation connected to the core (through the terminal residues) is referred to as the innermost interior generation. The outermost generation is referred to as the exterior layer. Thus, the dendrimer of the invention contains 1 to 8 generations of which 0 to 7 are interior generations emanating radially from the core and 1 is the exterior layer.

Each interior generation, when present, comprises 2 or more molecular units which independently are of the formula A:

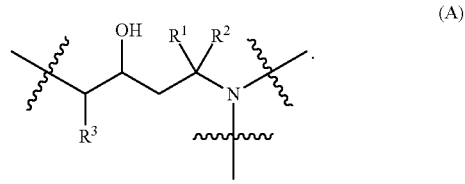

(A)

In some embodiments, one of $R^1$ and $R^2$ in the formula A molecule is hydrogen and the other is $C_1$-$C_{10}$ alkyl, alternatively $C_1$-$C_6$ alkyl, alternatively $C_1$-$C_3$ alkyl, alternatively ethyl, or alternatively methyl.

In some embodiments, $R^1$ and $R^2$ are either both hydrogen or both $C_1$-$C_{10}$ alkyl. In further embodiments, $R^1$ and $R^2$ are both $C_1$-$C_6$ alkyl, alternatively $C_1$-$C_3$ alkyl, alternatively ethyl, or alternatively methyl.

In some embodiments, $R^1$ and $R^2$, together with the carbon to which they are attached, form a $C_3$-$C_{12}$ cycloalkyl ring. In further embodiments, $R^1$ and $R^2$, together with the carbon to which they are attached, form a cyclohexyl ring.

In some embodiments, $R^3$ is H.

In some embodiments, the dendrimer comprises 0, alternatively 1, alternatively 2, alternatively 3, alternatively 4, alternatively 5, alternatively 6, or alternatively 7 interior generations. In some embodiments, the dendrimer comprises from 1 to 7 interior generations.

In some embodiments, all of the molecular units of formula A within a particular interior generation have the same chemical structure. In some embodiments, all of the molecular units of formula A in all interior generations have the same chemical structure.

In some embodiments, 2 or more of the molecular units of formula A within a particular interior generation or between interior generations, have differing chemical structures, e.g., R3 in one molecule differs from R3 in 1 or more of the other formula A molecules either in the same interior generation or in a different interior generation.

In some embodiments, the dendrimer comprises 1 generation. Thus, the dendrimer contains 0 (zero) interior generations.

The dendrimer comprises an exterior layer that is attached to the outermost of the interior generations or to the core through the terminal residues if no interior generations are present. The exterior layer comprises 2 or more molecular units independently having formula B:

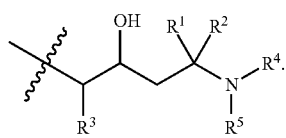
(B)

wherein $R^1$, $R^2$, and $R^3$ carry the same definitions as in the formula A molecule and $R^4$ and $R^5$ are each H, or $R^4$, $R^5$ and the nitrogen to which they are attached form a $NO_2$ group.

In some embodiments, $R^4$ and $R^5$ are each H.

In some embodiments, $R^4$, $R^5$ and the nitrogen to which they are attached form a $NO_2$ group.

In some embodiments, all of the molecular units of formula B within the exterior layer have the same chemical structure. In some embodiments, $R^1$, $R^2$, and $R^3$ in all of the molecular units of formula B are the same as $R^1$, $R^2$, and $R^3$ in all the interior generations if interior generations are present in the dendrimer.

In some embodiments, 2 or more of the molecular units of formula B within the exterior layer have differing chemical structures, e.g., $R^3$ in one molecule differs from $R^3$ in 1 or more of the other formula B molecules. In some embodiments, 1 or more of the molecular units of formula B have differing $R^1$, $R^2$, and/or $R^3$ groups to 1 or more of the formula A molecules (if interior generations are present in the dendrimer).

In some embodiments, when the core is derived from the dendrimer comprises at least 5 molecular units of formula A and/or formula B.

In some embodiments, the dendrimer may be represented by formula C:

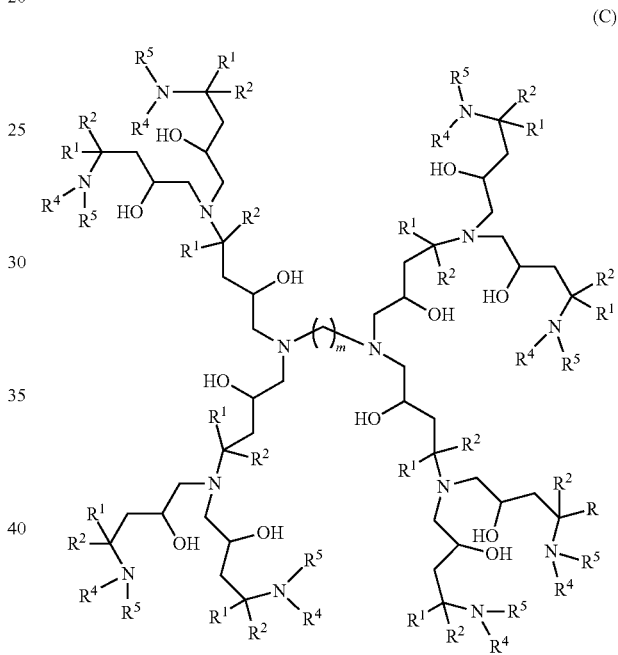
(C)

wherein m is an integer from 2 to 12, $R^1$ and $R^2$ are independently: H or $C_1$-$C_{10}$ alkyl or $R^1$ and $R^2$, together with the carbon to which they are attached, form a $C_3$-$C_{12}$ cycloalkyl ring optionally substituted with $C_1$-$C_6$ alkyl; and $R^4$ and $R^5$ are each H, or $R^4$, $R^5$ and the nitrogen to which they are attached form a $NO_2$ group.

In some embodiments of formula C, $R^1$ and $R^2$ are H at all occurrences.

In some embodiments of formula C, $R^1$ at all occurrences is H and $R^2$ at all occurrences is $C_1$-$C_6$ alkyl, alternatively $C_1$-$C_3$ alkyl, or alternatively ethyl or methyl.

In some embodiments of formula C, $R^1$ and $R^2$ at all occurrences, together with the carbon to which they are attached, form a cyclohexyl ring. In some embodiments of formula C, m is 6.

Exemplary dendrimers of the invention include the following Table 1:
TABLE 1
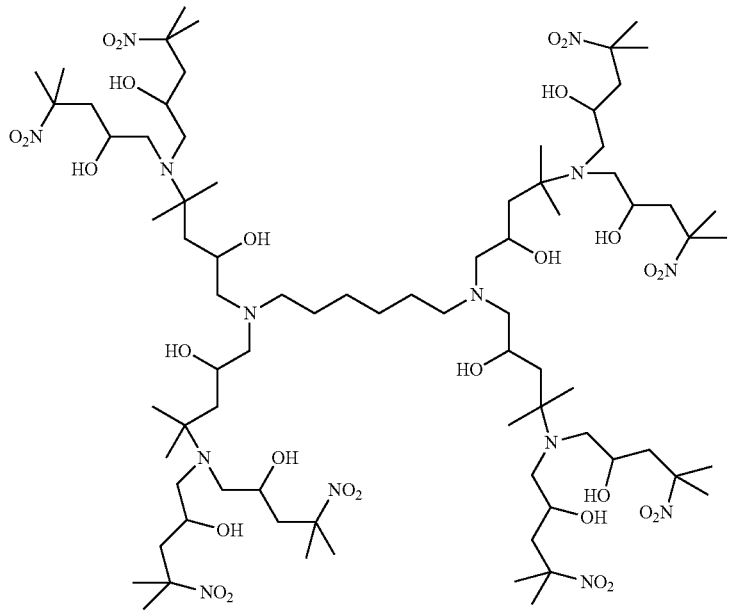 [SMILES: CC(C)(CC(O)CN(CCCCCCN(CC(O)CC(C)(C)N(CC(O)CC(C)(C)[N+](=O)[O-])CC(O)CC(C)(C)[N+](=O)[O-])CC(O)CC(C)(C)N(CC(O)CC(C)(C)[N+](=O)[O-])CC(O)CC(C)(C)[N+](=O)[O-])CC(O)CC(C)(C)N(CC(O)CC(C)(C)[N+](=O)[O-])CC(O)CC(C)(C)[N+](=O)[O-])N(CC(O)CC(C)(C)[N+](=O)[O-])CC(O)CC(C)(C)[N+](=O)[O-]]
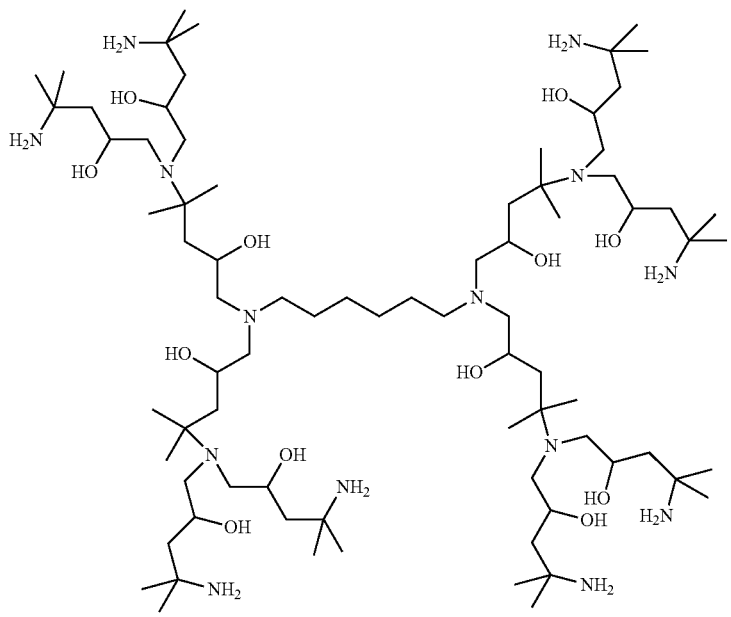 [SMILES: CC(C)(N)CC(O)CN(CC(O)CC(C)(C)N)C(C)(C)CC(O)CN(CCCCCCN(CC(O)CC(C)(C)N(CC(O)CC(C)(C)N)CC(O)CC(C)(C)N)CC(O)CC(C)(C)N(CC(O)CC(C)(C)N)CC(O)CC(C)(C)N)CC(O)CC(C)(C)N(CC(O)CC(C)(C)N)CC(O)CC(C)(C)N]

TABLE 1-continued
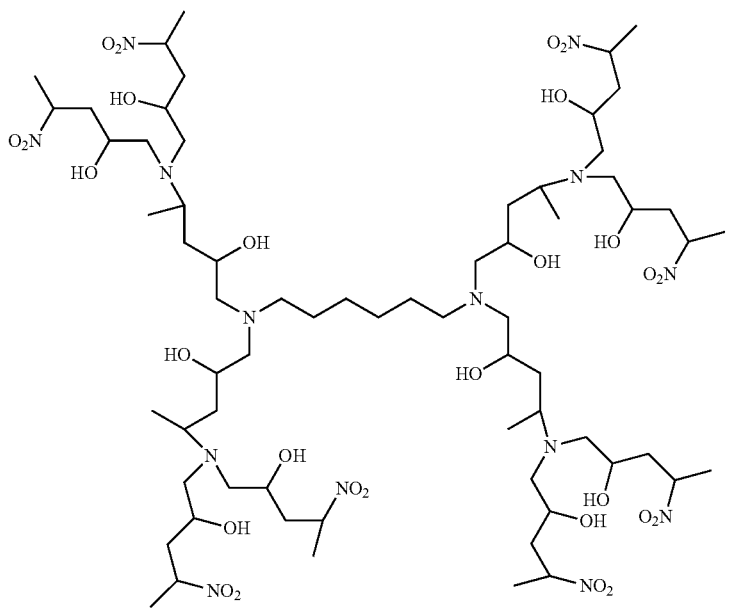
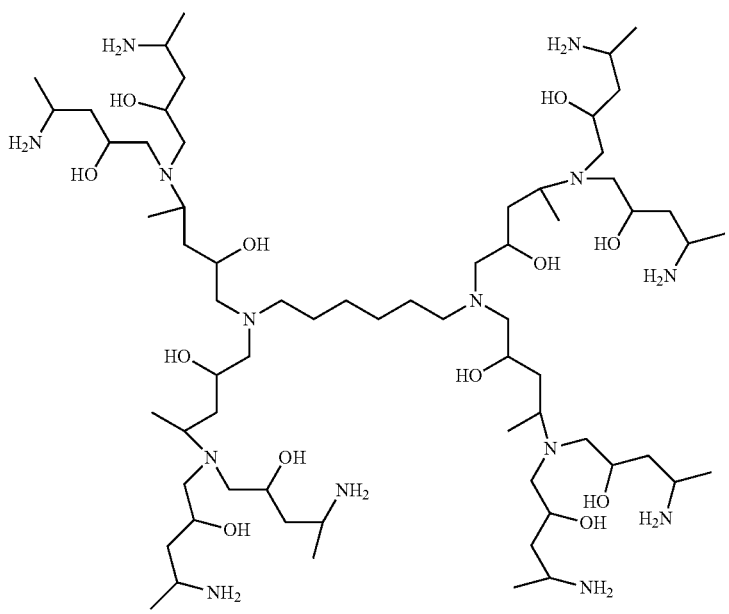
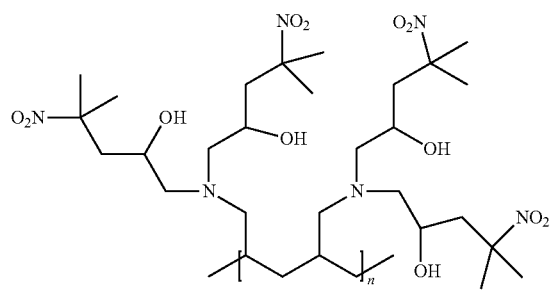
wherein n is 100 to 1500

TABLE 1-continued
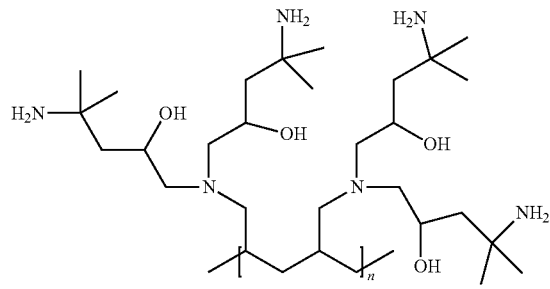
wherein n is 100 to 1500
Generation 1 from poly(allylamine)
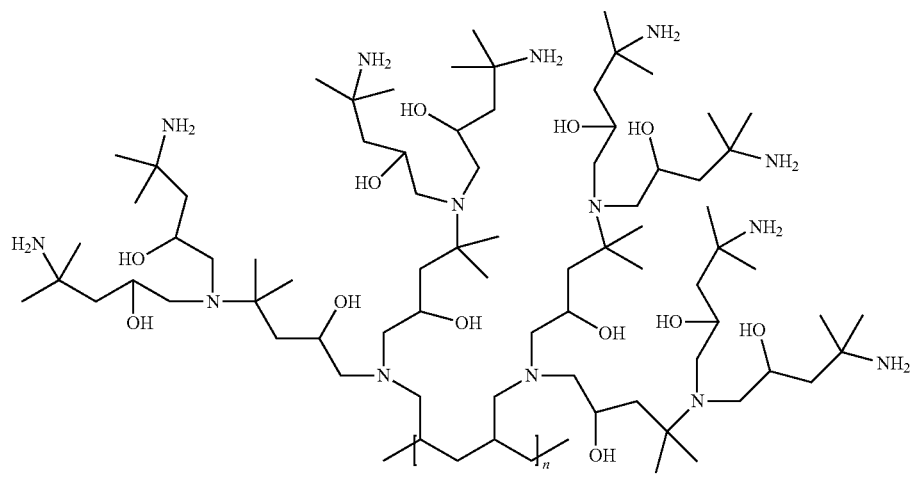
wherein n is 100 to1500
Generation 2 from poly(allylamine)
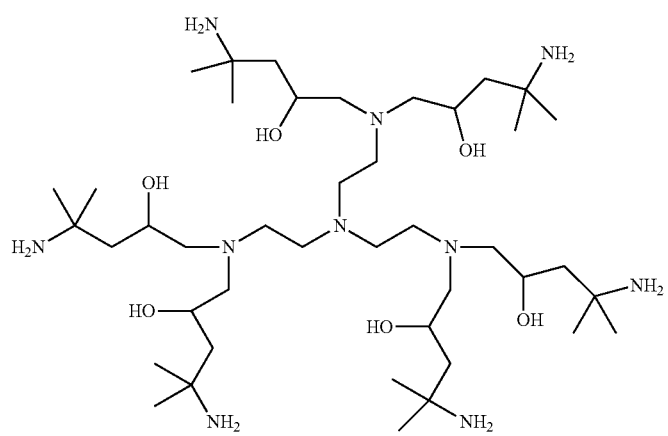 [SMILES: CC(C)(N)CC(O)CN(CCN(CCN(CC(O)CC(C)(C)N)CC(O)CC(C)(C)N)CCN(CC(O)CC(C)(C)N)CC(O)CC(C)(C)N)CC(O)CC(C)(C)N]
Generation 1 from tris(aminoethyl)amine TABLE 1-continued

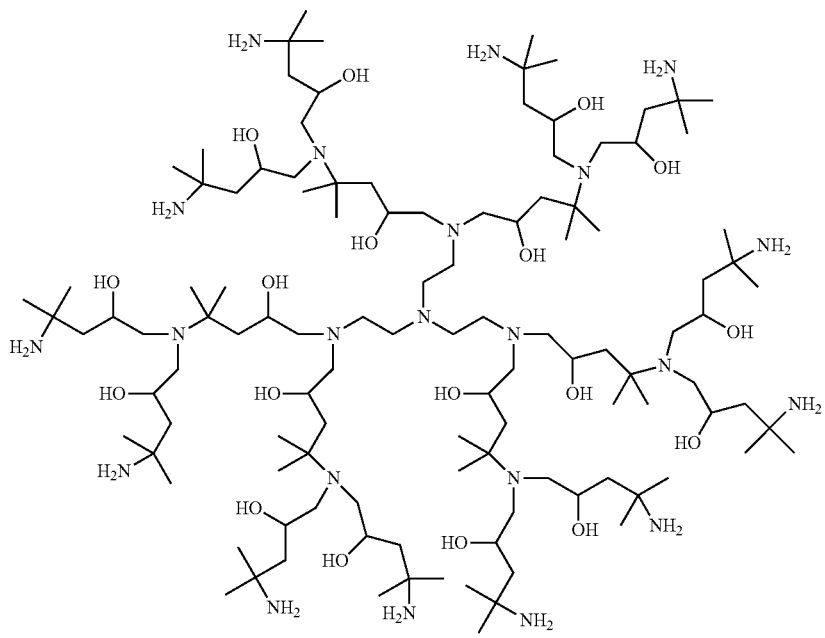 [SMILES: CC(C)(N)CC(O)CN(CC(O)CC(C)(C)N)C(C)(C)CC(O)CN(CCN(CCN(CC(O)CC(C)(C)N(CC(O)CC(C)(C)N)CC(O)CC(C)(C)N)CC(O)CC(C)(C)N(CC(O)CC(C)(C)N)CC(O)CC(C)(C)N)CCN(CC(O)CC(C)(C)N(CC(O)CC(C)(C)N)CC(O)CC(C)(C)N)CC(O)CC(C)(C)N(CC(O)CC(C)(C)N)CC(O)CC(C)(C)N)CC(O)CC(C)(C)N(CC(O)CC(C)(C)N)CC(O)CC(C)(C)N]

Generation 2 from tris(aminoethyl)amine

The dendrimers may be prepared through the reaction of a polyvalent organic molecule with a nitroalkyloxirane compound. The polyvalent organic molecule comprises a core to which are connected 2 or more functional groups capable of reacting with the oxirane ring of the nitroalkyloxirane compound. In some embodiments, the terminal functional groups may be amines, hydroxyls, thiols, or combinations of two or more thereof.

The structure of the polyvalent organic molecule is not critical to the invention, and it can be any compound, including polymers, capable of reacting with an epoxide. A wide variety of materials may be suitably used. By way of non-limiting example, the polyvalent organic molecule may, for instance, be an alicyclic or an aliphatic acyclic compound, an aryl compound, a heterocyclic compound containing N, O, and/or S atoms, or compounds containing combinations of such groups, or a polymer, each further containing 2 or more functional groups.

Additional non-limiting examples include: ethylene diamine, ammonia, hexamethylenediamine, piperazine, Jeffamines (Huntsman Chemicals), phenol, bisphenol-A, methylene-bisphenol, tri-(hydroxymethyl)methane, tris(aminoethyl)amine, pentaerythritol, amino-acids such as cysteine and lysine, polymers such as polylysine, polyethyleneimine and polyallylamine.

In some preferred embodiments, the polyvalent organic molecule is an aliphatic acyclic compound that is a $C_1$-$C_{10}$ alkyl, alternatively $C_2$-$C_8$ alkyl, or alternatively $C_3$-$C_6$ alkyl substituted with 2 to 4, preferably 2, terminal functional groups.

In some further preferred embodiments, the polyvalent organic molecule is an aliphatic acyclic diamine compound. Examples include compounds of the formula $H_2N$—$(CH_2)_n$—$NH_2$, wherein n is 2 to 12, alternatively 2 to 10, alternatively 2 to 6. In some embodiments, the polyvalent organic molecule is hexane-1,6-diamine. Polyvalent organic molecules suitable for use in the invention are commercially available and/or may be readily prepared by those skilled in the art.

As noted above, in some embodiments, when the core of the dendrimer is an aliphatic acyclic residue containing 2 amine residues, then the dendrimer comprises at least 2 generations. Thus, for instance, in some embodiments the dendrimer contains at least two generations when the polyvalent organic molecule from which the core is derived is an amine compound of the formula $HNR^{10}R^{11}$. $R^{11}$ is H, or $C_1$-$C_{10}$ alkyl optionally substituted with hydroxy; and $R^{10}$ is H, $C_1$-$C_{10}$ alkyl optionally substituted with hydroxy, or —(C($R^6$)($R^7$))$_t$—N($R^{12}$)($R^{13}$), wherein t is an integer from 1 to 6, and $R^6$ and $R^7$ are independently H or $C_1$-$C_{10}$ alkyl, and $R^{12}$ and $R^{13}$ are independently H or $C_1$-$C_{10}$ alkyl optionally substituted with hydroxy.

The nitroalkyloxirane monomer used in the reaction with the polyvalent organic molecule is a compound of the formula III:

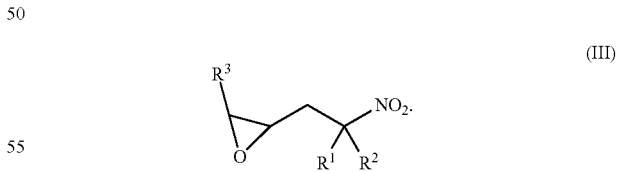

(III)

wherein $R^1$ and $R^2$ are independently H or $C_1$-$C_{10}$ alkyl, or $R^1$ and $R^2$, together with the carbon to which they are attached, form a $C_3$-$C_{12}$ cycloalkyl ring optionally substituted with $C_1$-$C_6$ alkyl, and $R^3$ is H, $C_1$-$C_{10}$ alkyl, or phenyl. In some embodiments, $R^1$ and $R^2$ are either both hydrogen or both $C_1$-$C_{10}$ alkyl. In further embodiments, $R^1$ and $R^2$ are both $C_1$-$C_6$ alkyl, alternatively $C_1$-$C_3$ alkyl, or alternatively methyl. In some embodiments, $R^1$ and $R^2$, together with the carbon to which they are attached, form a $C_3$-$C_{12}$ cycloalkyl ring. In further embodiments, $R^1$ and $R^2$, together with the carbon to which they are attached, form a cyclohexyl ring. In some embodiments, $R^3$ is H. In some embodiments, the compound is 2-(2-methyl-2-nitropropyl)oxirane Compounds of formula III may be prepared by the epoxidation of the corresponding nitrated alkene, which may itself be purchased or prepared, for instance, by palladium catalyzed allylation of a nitroalkane. For the conversion of the alkene to the formula III compound, any epoxidation reagent capable of oxidizing an alkene to an epoxy group may be used. Typical epoxidation reagents include meta-chloroperoxybenzoic acid (m-CPBA), oxone, and hydrogen peroxide. A convenient epoxidation reagent is m-CPBA. Typically, the reaction is conducted under inert atmosphere and in the presence of a solvent, such as methylene chloride. An excess of the epoxidation reagent may be used. The reaction may be conducted at a temperature between about 0 and about 55° C., preferably 0 to 45° C. Following sufficient time for reaction to occur, e.g., 1 to 6 hours, the desired product may be isolated or purified using known techniques.

According to the invention, the polyvalent organic molecule and the nitroalkyloxirane compound of formula III are combined in sufficient amount such that the nitroalkyloxirane compound reacts with the terminal functional groups of the polyvalent organic molecule to form a nitro compound. The nitro compound comprises a core and a plurality of molecular units connected to the core and independently having formula B-1:

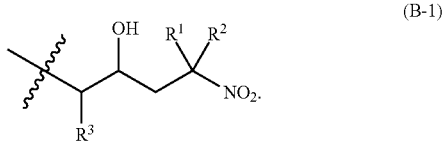

(B-1)

The reaction of the polyvalent organic molecule with the nitroalkyloxirane compound may be carried out, for instance, by mixing the reactants and then heating at elevated temperature, such as at 50-80° C., for sufficient time for the ring opening of the epoxide to occur, such as 1 to 12 hours. A solvent may optionally be used. Following reaction, the nitro compound product may be purified or isolated from the reaction mixture using techniques well known to those skilled in the art. A common method for purification involves dissolving the crude mixture in a suitable solvent, such as methanol, and using a membrane to purify the product by tangential flow filtration. Alternatively, the nitro compound may be used without isolation and/or purification.

The nitro compound may then be reduced to form an amine compound comprising the core and a plurality of molecular units connected to the core and independently having formula B-2:

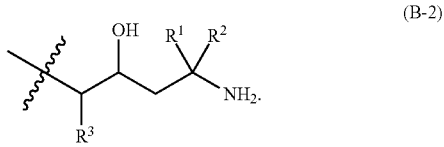

(B-2)

The conversion of the nitro compound to the amine compound may be carried out via reduction using any reagent capable of reducing aliphatic nitro groups. Examples of such reducing agents include hydrogen gas in combination with a catalyst, for example, Raney nickel or a platinum or palladium based catalyst (Pt or Pd in elemental form or as oxides, with or without supports, e.g., carbon); and other reducing agents including metal/acid combinations, e.g., iron/acetic acid; aluminum hydrides, e.g., VITRIDE. Preferred reducing agents include hydrogen gas in combination with any of the following catalysts: Raney nickel, platinum, or palladium. Conditions for hydrogenation of nitro groups are well known, e.g., a temperature range of about 20-80° C. at a pressure of about 100-1000 psi (690 kPa-6900 kPa) are typical, although these can be readily adjusted by one skilled in the art.

In the invention process, the amine compound prepared in the preceding step is optionally reacted with additional nitroalkyloxirane compound of formula III, followed optionally by reduction, until a dendrimer of the desired number of generations is formed. It should be noted that following the final generation-adding reaction the reduction step is optional. In the invention, when the polyvalent organic molecule from which the core is derived is hexane-1,6-diamine, the dendrimer contains at least two generations.

The dendrimer compounds described herein have a variety of uses. For instance, they may be complexed with small molecules (for example pharmaceuticals for applications of drug delivery) or metals for catalysis. Applications therefore include, for instance, drug delivery, diagnostics, use as transfection agents, use as catalyst supports and as viscosifiers. Additional complexation versatility for these and other applications can be incorporated into the dendrimer when the nitroalkyloxirane monomer used for the synthesis has either of $R^1$ or $R^2$ as H, e.g. 4-nitro-1,2-epoxyhexane, which may be prepared from 1-nitropropane.

A dendrimer of the invention having nitro terminal groups (i.e., $R^4$, $R^5$ and the nitrogen to which they are attached form a $NO_2$ group), in addition to reduction to the amine, can also be further functionalized using typical nitro-alkane chemistry familiar to those skilled in the art. Examples of such chemistry include: base catalyzed reaction of the nitroalkane portions of the dendrimer with an aldehyde (Henry Reaction); base catalyzed reaction of the nitroalkane with for example an α,β-unsaturated ester or nitrile e.g. methyl acrylate or acrylonitrile (Michael Reaction), base catalyzed reaction of the nitroalkane with an aldehyde in the presence of an amine (Mannich Reaction), strong base (e.g. butyl lithium) catalyzed reaction of the nitroalkane with an alkyl halide e.g. methyl iodide (alkylation), strong base catalyzed (e.g. butyl lithium) reaction of the nitroalkane with an acyl chloride or other activated ester, e.g. N-hydroxysuccinimide ester (acylation), or base catalyzed halogenation of the nitroalkane to form an α-halonitro-derivative.

A dendrimer of the invention having amine terminal groups (i.e., $R^4$ and $R^5$ are H), may further be functionalized using typical amine chemistry familiar to those skilled in the art. Examples of such chemistry include: reacting the amine with an epoxide, acrylate, acid chloride and the like in order to functionalize the surface as desired. A dye, a drug, a drug targeting moiety etc. may then be attached to the molecule.

Non-limiting examples of a further functionalized dendrimer is shown in Table 2:
TABLE 2
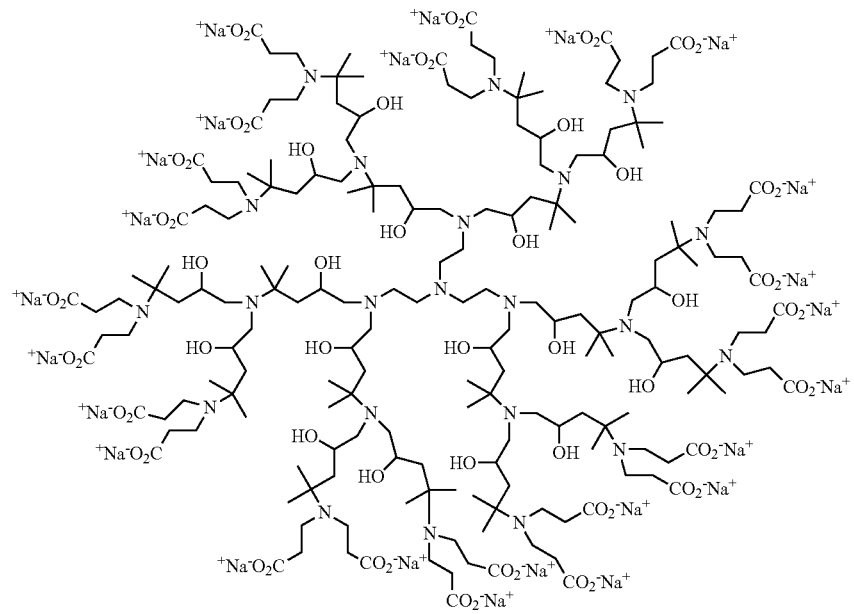
Generation 2 from tris(aminoethylamine) terminated with sodium acrylate
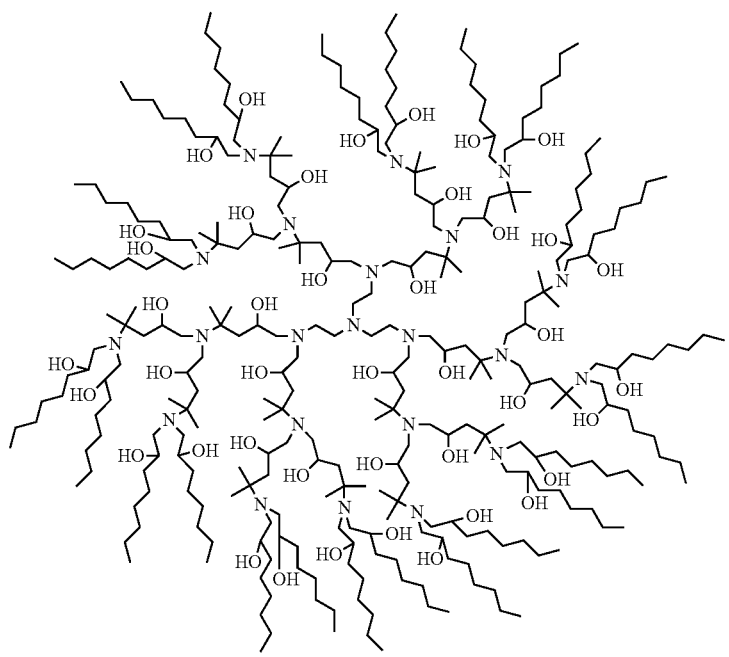
hydrophobically modified Generation 2 Dendrimer Some embodiments of the invention will now be described in detail in the following Examples.

EXAMPLES

Example 1

Two Generation Amine Dendrimer

Step A. Preparation of 4-methyl-4-nitropent-1-ene

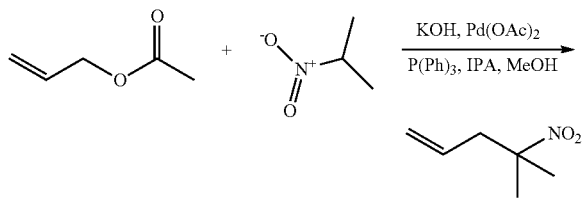

(1)

A 3 neck 500 mL round bottom flask equipped with dropping funnel, temperature controller, nitrogen outlet, stir bar and condenser is charged with 17.3 g (0.309 mols) of potassium hydroxide (KOH), 50 mL of methanol and 150 mL of isopropanol. The addition takes place at room temperature, however, while the base is dissolving in the solvent there is a 20° C. increase in temperature. The base solution is allowed to stir under nitrogen for 20 minutes and during that period, the temperature of the flask goes down to 35° C. To the above base solution, 25 g of 2-nitropropane ("2-NP") (0.281 mols) is added slowly with vigorous stirring of the mixture. The mixture is stirred for 10 minutes and palladium acetate (0.56 mmol)/triphenyl phosphine (1.7 mmol) added as catalyst. The resulting yellow solution is stirred under nitrogen for another 5 minutes and 30.9 g of allyl acetate added drop-wise to the mixture via the dropping funnel. During the addition of the acetate, the reaction mixture turns dark and cloudy, followed by dark brown to clear orange and finally clear yellow upon completion of addition. During the addition, the temperature rises to about 60° C. At this point, heat is switched on and the mixture stirred for 6 h at 60° C. followed by overnight stirring at room temperature. The next day the mixture is heated again to 60° C. followed by room temperature stirring overnight. The total reaction time is 48 h.

After the reaction is complete, the contents of the flask are poured into a separatory funnel containing 300 mL of water. The organic layer is extracted with pentane (3×150 mL) and dried under MgSO$_4$. Excess solvent is stripped off under a rotary evaporator. The solution is purified by vacuum distillation at 25 mmHg, which results in 17 g (53%) of 4-methyl-4-nitropent-1-ene as colorless solution at 96-98% purity. The retention time of the alkene on the GC is 7.4 minutes. GC/MS analysis shows [MH]$^+$ m/z 83. $^1$H NMR (CDCl$_3$): ∂ 0.91 (s, 6 H), ∂ 2.63 (d, 2 H), ∂ 5.07-5.17 (m, 2 H) and ∂ 5.59 (m, 1 H). $^{13}$C NMR (CDCl$_3$): ∂ 25.3, 44.8, 87.6, 120 and 131 ppm.

Step B. Preparation of 2-(2-methyl-2-nitropropyl)oxirane

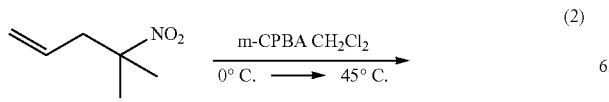

(2)

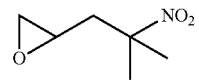

A 3 neck 100 mL round bottom flask equipped with dropping funnel, temperature controller, nitrogen outlet, stir bar and condenser is charged with 1.54 g (11 mmol) of alkene and 15 mL of CH$_2$Cl$_2$. To the solution, 2.68 g (16 mmol) of MCPBA dissolved in 25 mL CH$_2$Cl$_2$ is added slowly. After complete addition, the reaction is refluxed for 6 hrs and progress of the reaction monitored by GC. After 6 h, there is about 80% conversion to the epoxide. The reaction is cooled to room temperature and the solid MCPBA that crashes out of solution removed by gravity filtration. The yellow filtrate is placed in the flask again and 0.3 mol equivalent of the MCPBA in CH$_2$Cl$_2$ solution is added to the flask. The mixture is refluxed again for 2 hrs and at this point, resulting in 100% conversion to the epoxide. The reaction mixture is cooled to room temperature and excess MCPBA removed by gravity filtration. The organic layer is washed with 10% Na$_2$CO$_3$ (3×15 mL) followed by brine (3×15 mL). The organic layer is dried under MgSO$_4$ and excess solvent stripped off under rotary evaporator. This affords 0.73 g (50%) of pure epoxide. The retention time of the epoxide on the GC is 11.0 minutes. $^1$H NMR (CDCl$_3$): ∂ 1.62 (s, 6H), ∂ 1.96 (m, 2H), ∂ 2.32 (m, 1 H), ∂ 2.53 (m, 1 H) and ∂ 2.97 (m, 1 H). $^{13}$C NMR (CDCl$_3$): ∂ 25.3, 26.9, 43.3, 46.0, 47.9 and 87.0 ppm.

Step C. Reaction of 2 with hexane-1,6-diamine to Make Compound (3)

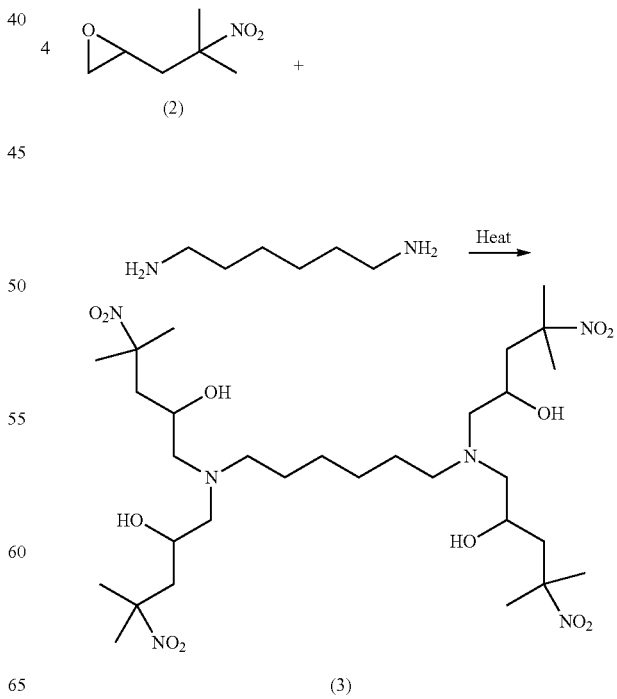

(3)

A one neck 50 mL round bottom flask equipped with a stir bar, condenser and nitrogen outlet is charged with 4.60 g (0.03 mols) of 2-(2-methyl-2-nitropropyl)oxirane and 0.85 g (0.007 mols) of hexane-1,6-diamine. The reaction mixture is stirred at room temperature for 30 minutes followed by heating at 80° C. for 8-10 h. The yellow color oxirane turns to dark brown and the resulting product has high viscosity. GC analysis of the resulting mixture shows the starting materials are consumed during the 8-10 h reaction time. The nitro amine products are too large to show up on the GC-MS and the reaction was deemed complete once the starting material peaks in the GC disappeared. The resulting dark brown high viscous material is taken as-is to the hydrogenation step. Alternatively, compound (3) can be prepared as follows:

A one neck 50 mL round bottom flask equipped with a stir bar, condenser and nitrogen outlet is charged with 1.5 g (0.012 mols) of hexane-1,6-diamine and 7 mL methanol. The mixture is stirred until all the diamines dissolves. To this is added, 7.5 g (0.052 mols) of 2-(2-methyl-2-nitropropyl)oxirane. The reaction mixture is stirred at room temperature for 30 minutes followed by reflux for 16 h. The yellow color oxirane turns to dark brown. GC analysis of the resulting mixture shows the starting materials are consumed during the 16 h reaction time. The nitro amine products are too large to show up on the GC-MS and the reaction was deemed complete once the starting material peaks in the GC disappeared. The resulting dark brown high viscous material is taken as-is to the hydrogenation step.

Step D. Hydrogenation of Compound (3) to Prepare Compound (4)

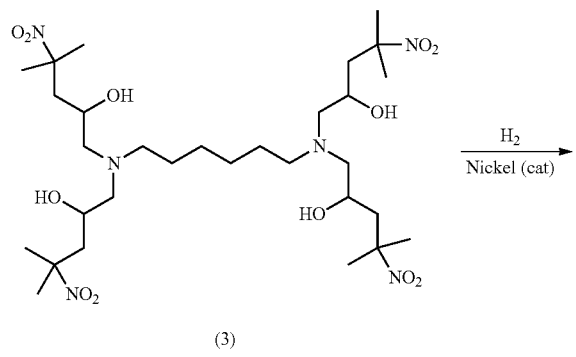

(3)

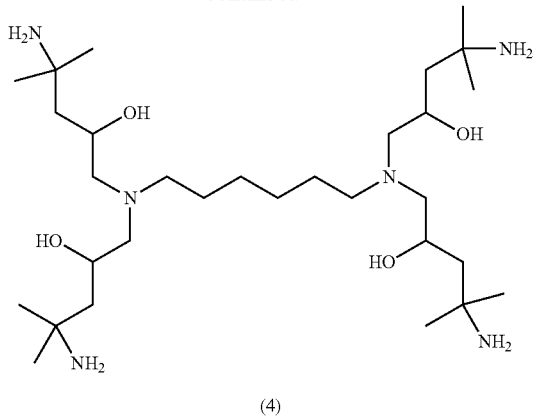

(4)

A 300 mL Parr autoclave is charged with methanol (150 mL), Raney Nickel catalyst (R-3111, 5.0 g wet weight) and compound (3) (5 g crude) dissolved in 50 mL MeOH. The reactor is sealed, purged with nitrogen followed by purging with hydrogen and then brought up to 60° C. under 450 psi hydrogen pressure. When the temperature reaches 60° C., the reactor pressure is increased to approximately 750 psi. The reaction is stopped when no more hydrogen is consumed in the reaction. The entire reaction takes 2-2.5 h to reach completion. After cooling to room temperature, the reactor is vented, opened and the catalyst isolated via vacuum filtration. The brown filtrate is stripped on a rotary evaporator (50-55° C./28-29" vacuum) to remove water/methanol. The above process provides 3.8 g of the crude mixture. The material is too large to elute and characterize by GC/MS. Therefore, compound (4), 1,1',1",1'''-(hexane-1,6-diylbis(azanetriyl)) tetrakis(4-amino-4-methylpentan-2-ol) is identified by LC/MS with [M+H]=577. The main impurities in the sample are the ones carried over during the synthesis of 2-(2-methyl-2-nitropropyl)oxirane.

Step E. Reaction of Compound (4) with 2-(2-methyl-2-nitropropyl)oxirane (2) to Prepare Compound (5)

1 mole of Compound 4 is reacted with 8 moles of oxirane 2 following essentially the same procedure as described in Step C above.

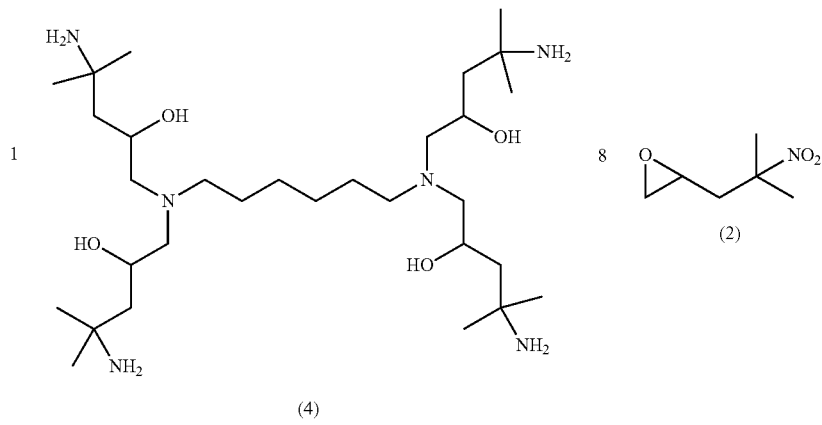

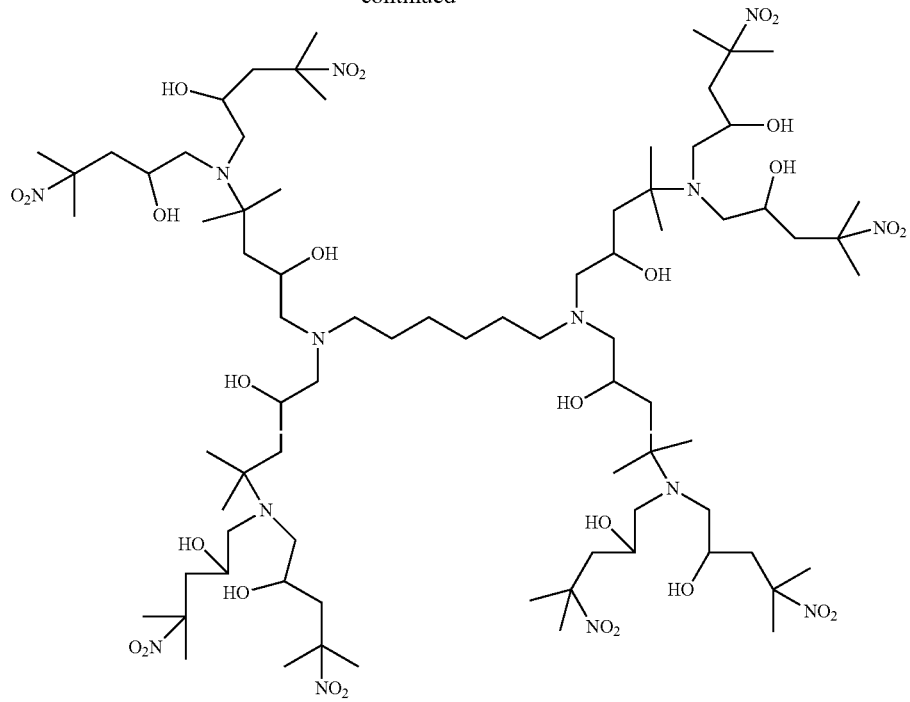

(5)

A one neck 50 mL round bottom flask equipped with a stir bar, condenser and nitrogen outlet is charged with 5.1 g (80% Purity, 0.028 mols, 8.1 equivalents) of 2-(2-methyl-2-nitropropyl)oxirane, 2 g (0.0034 mols, 1 equivalent) of 1,1',1'',1'''-(hexane-1,6-diylbis(azanetriyl))tetrakis(4-amino-4-methylpentan-2-ol), Compound (4). and 10 mL of methanol. The reaction mixture is stirred at room temperature for 10 minutes followed by reflux for 16 h. The resulting product has high viscosity and deep brown in color. The reaction was deemed complete when the area percent of compound (2) didn't significantly decrease with time and further heating. The resulting dark brown high viscous material is further dissolved in additional methanol and taken as-is to the hydrogenation step.

Step F. Reduction of Compound (5) to Make the Amine Derivative, Compound (6)

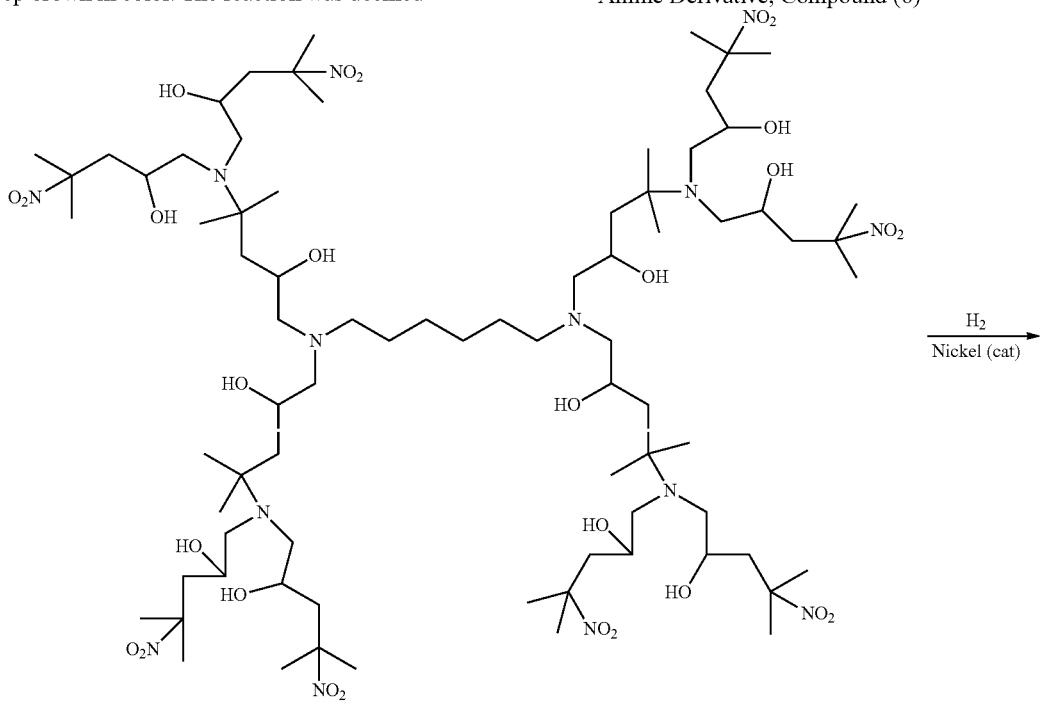

(5)

-continued

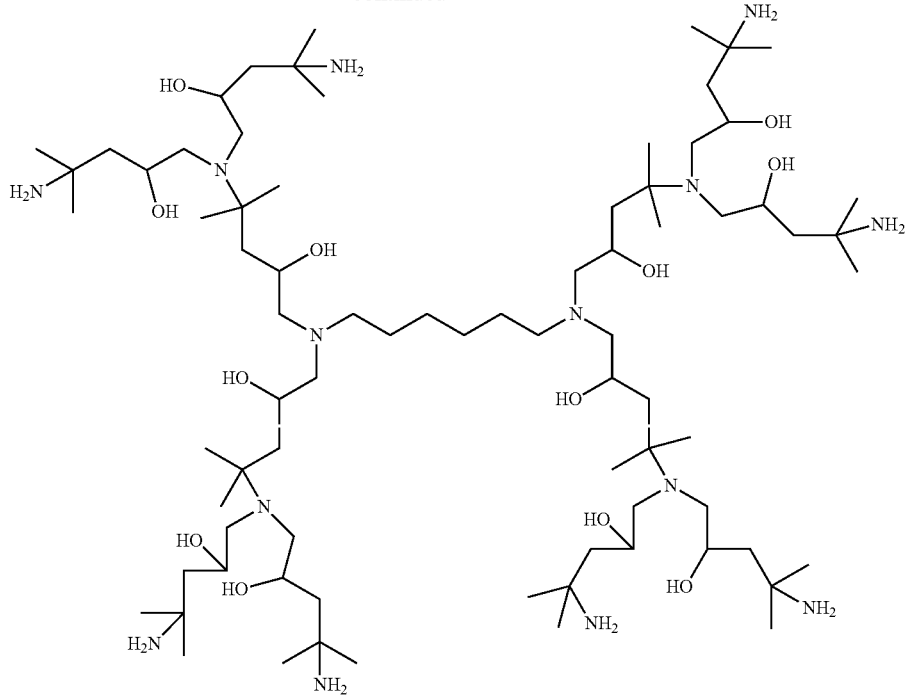

(5)

A 300 mL Parr autoclave is charged with methanol (100 mL), Raney Nickel catalyst (R-3111, 6.8 g wet weight) and compound 5 (~5 g crude) dissolved in 25 mL MeOH. The reactor is sealed, purged with nitrogen followed by purging with hydrogen and then brought up to 65° C. under 400 psi hydrogen pressure. When the temperature reaches 65° C., the reactor pressure is increased to approximately 650 psi. The reaction was run at 65° C. for 3 h, followed by increase in temperature to 70° C. for 25 min. The reaction is stopped when no more hydrogen is consumed in the reaction. The entire reaction takes approximately 3.5 h to reach completion. After cooling to room temperature, the reactor is vented, opened and the catalyst isolated via vacuum filtration. The brown filtrate is stripped on a rotary evaporator (50-55° C./28-29" vacuum) to remove water/methanol. The above process provides 1.8 g of the crude mixture. The mixture is analyzed by LC-MS. The analysis shows the presence of the desired product i.e., Compound (6) with [M+H]=1498, along with the products resulting from partial alkylation of compound (4) in Step E (n=3, 4, 5, 6 & 7 were detected). Further optimization of step E is possible to increase the purity of the desired product.

Example 2

Prophetic

Preparation of Generation 1 from Tris(Aminoethyl)Amine

In a 50 mL single neck round bottomed flask, equipped with a magnetic stirrer, reflux condenser and a nitrogen outlet, charge 1.5 g (0.01 mols) of tris(2-aminoethyl)amine and 10 mL of methanol. To this stirred solution is added 9.44 g (0.065 mols, 6.5 meq) of 2-(2-methyl-2-nitropropyl)oxirane and the mixture is stirred at ambient temperatures for about thirty minutes and is then heated at reflux for approximately 16 hours or until the starting materials are all consumed, e.g., as determined by GC analysis. The resulting product may be taken forward to the hydrogenation step with no further purification.

A 300 mL Parr autoclave is charged with methanol (150 mL), Raney Nickel catalyst (R-3111, 5.0 g wet weight) and the product from above after dilution further with methanol (50 mL). After sealing the reactor, purge with nitrogen followed by hydrogen and then warm to 60° C. under an atmosphere of hydrogen (450 psi). Once the reactor has reached a stable temperature of 60° C. the pressure can be increased to 750 psi of hydrogen and the reaction is monitored for hydrogen uptake. When no more hydrogen is being consumed (typically 2-2.5 h) the reaction is allowed to cool to ambient temperatures and is vented, opened and the catalyst is isolated via vacuum filtration. The solution can be concentrated on the rotary evaporator to a crude product.

This crude product can be optionally purified by cross flow filtration. Dissolving the crude product in methanol (approximately 200 mL) and concentrating with a suitable reverse osmosis membrane (e.g. Filmtec FT-30 membrane) in a flat cell (e.g. Amicon TC1R thin channel separator) will separate the majority of small molecular weight impurities from the dendrimer. When the solution containing the dendrimer is approximately 50 mL in volume the sample can be analyzed for low molecular weight volatile products by GC. When no further volatile products are observed by GC the product solution can be concentrated on a rotary evaporator and the material used without further purification.

Example 3

Prophetic

Preparation of Generation 2 from Tris(Aminoethyl)Amine

Following the same procedure as outlined for the Generation 1 material, 4.5 g (0.0054 mols) dissolved in approximately 15 mL of methanol can be reacted with 10.1 g (0.07 moles, 12.9 meq) of 2-(2-methyl-2-nitropropyl)oxirane. The reaction can be monitored by GC for consumption of the oxirane.

The crude product is similarly hydrogenated to the generation 2 amine terminated product by hydrogenation in methanol as described above, using Raney Nickel (R-3111) as a catalyst. Crude generation 2 dendrimer may be isolated as a crude yield. As described above this can be optionally purified further by cross flow filtration to remove all the low molecular weight impurities coming from the slight excess of oxirane used in the synthesis prior to further synthesis.

ent temperatures for 48 hours, the solvent and excess methyl acrylate can be removed by rotary evaporation, maintaining the temperature below 40° C., to provide crude product.

Dissolve the crude product in approximately 100 mL of methanol and with vigorous stirring slowly add approximately 9.6 mL of a 10% solution of sodium hydroxide to the mixture and stir at ambient temperatures for 24 hours. At the end of the reaction, the solution pH should be approximately 9.5. The solution can be tested by IR spectroscopy to monitor the hydrolysis of the ester functionality. Once all the ester has been hydrolyzed, the solvent can be removed by rotary evaporation. Residual water can be removed by azeotropic distillation with toluene to provide a yellow oil. If a solid is required, the product can be isolated as a powder by redissolving and precipitating carefully by the slow addition of diethyl ether with vigorous stirring.

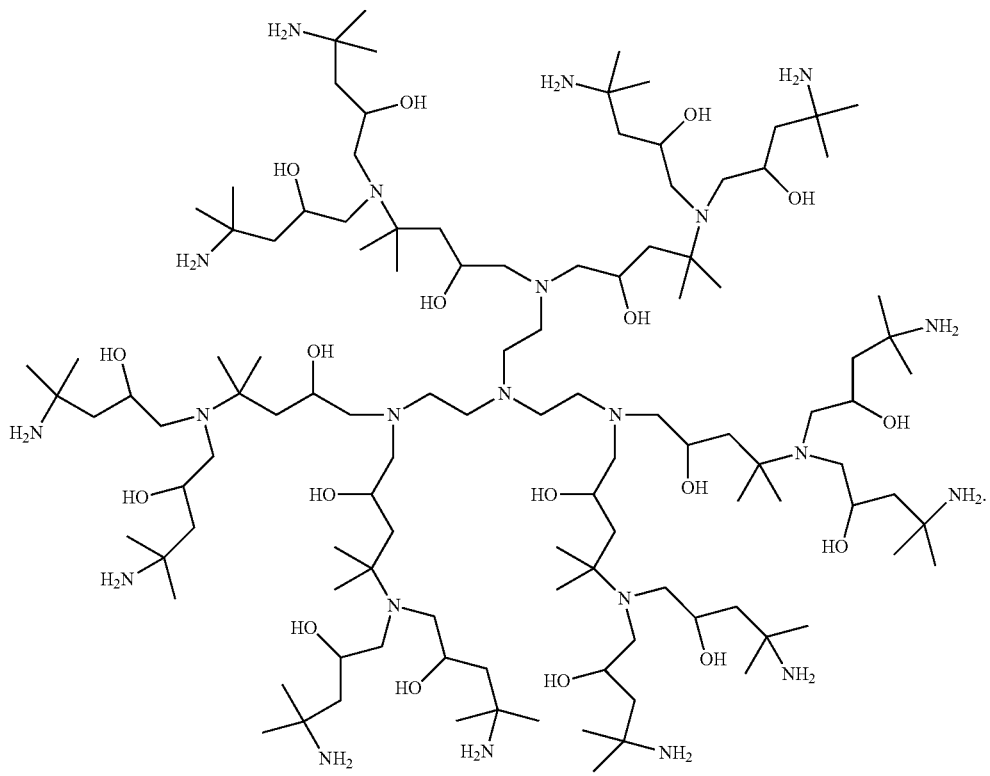 [SMILES: CC(C)(N)CC(O)CN(CC(O)CC(C)(C)N)C(C)(C)CC(O)CN(CCN(CCN(CC(O)CC(C)(C)N(CC(O)CC(C)(C)N)CC(O)CC(C)(C)N)CC(O)CC(C)(C)N(CC(O)CC(C)(C)N)CC(O)CC(C)(C)N)CCN(CC(O)CC(C)(C)N(CC(O)CC(C)(C)N)CC(O)CC(C)(C)N)CC(O)CC(C)(C)N(CC(O)CC(C)(C)N)CC(O)CC(C)(C)N)CC(O)CC(C)(C)N(CC(O)CC(C)(C)N)CC(O)CC(C)(C)N]

Example 4

Prophetic

Preparation of Methyl Propionate Dendrimer from Tris(2-aminoethyl)amine

In a 50 mL round bottomed flask, charge methyl acrylate, 2.32 g (0.027 mol, 26 meq), separately dissolve the Generation 2 dendrimer synthesized from tris-(2-aminoethyl)amine) (Example 3), 2.5 g (0.001 mol) and methanol 25 mL and slowly add this over approximately two hours with vigorous stirring to the methylacrylate solution. After stirring at ambi-

Example 5

Prophetic

Preparation Hydrophobically Modified Generation 2 Dendrimer by Reaction with Epoxyoctane To a solution of 2.5 g (0.001 mol) of the generation 2 dendrimer initiated from tris-(2-aminoethylamine) (Example 3) dissolved in methanol 25 mL, add 3.15 g of epoxyoctane (0.027 mol) and stir the reaction at room temperature for about six days. The consumption of the epoxyoctane can be monitored by GC and the reaction can be accelerated by heating at 60° C. if desired. Removal of the solvent by rotary evaporation will result in a crude product that may be further purified by known techniques.

What is claimed is:

1. A dendrimer comprising:
   a core comprising 2 or more terminal residues and derived from a polyvalent organic molecule;
   from 1 to 8 generations emanating radially from the core, the 1 to 8 generations comprising:
   from 0 to 7 interior generations comprising 2 or more molecular units independently having formula A:

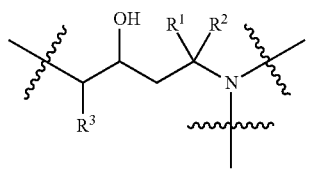

(A)

wherein $R^1$ and $R^2$ are independently H or $C_1$-$C_{10}$ alkyl, or $R^1$ and $R^2$, together with the carbon to which they are attached, form a $C_3$-$C_{12}$ cycloalkyl ring optionally substituted with $C_1$-$C_6$ alkyl, and $R^3$ is H, $C_1$-$C_{10}$ alkyl, or phenyl, and wherein the innermost interior generation is attached to the core through the terminal residues;
an exterior layer attached to the outermost of the interior generations or to the core through the terminal residues if no interior generations are present, the exterior layer comprising 2 or more molecular units independently having formula B:

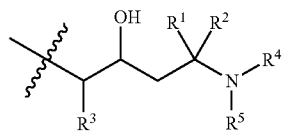

(B)

wherein $R^4$ and $R^5$ are each H, or $R^4$, $R^5$ and the nitrogen to which they are attached form a $NO_2$ group,
wherein the terminal residues are amine residues.

2. The dendrimer of claim 1 wherein $R^1$ and $R^2$ are each $C_1$-$C_{10}$ alkyl.

3. The dendrimer of claim 1 wherein $R^3$ is H.

4. The dendrimer of claim 1 wherein when the core is an aliphatic acyclic residue containing 2 amine residues, the dendrimer comprises at least 2 generations.

5. The dendrimer of claim 1 of the structure:

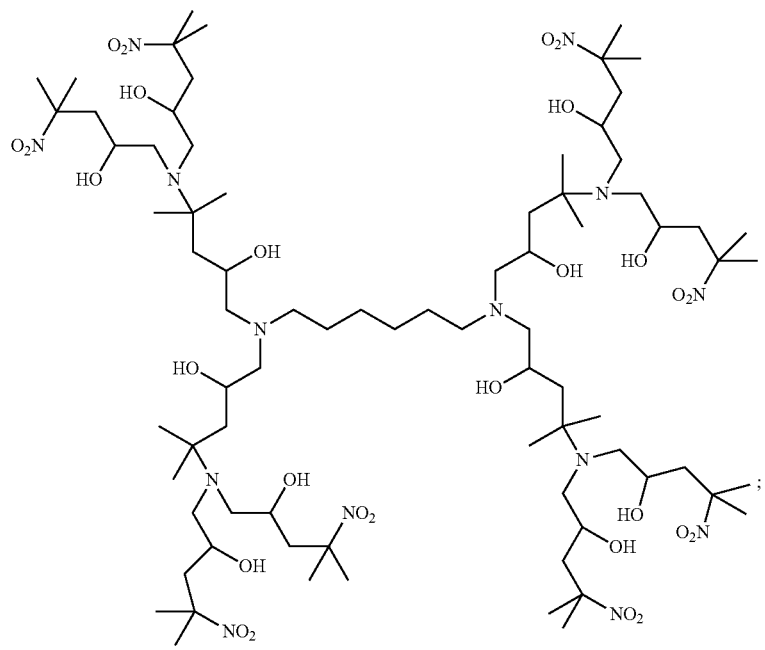

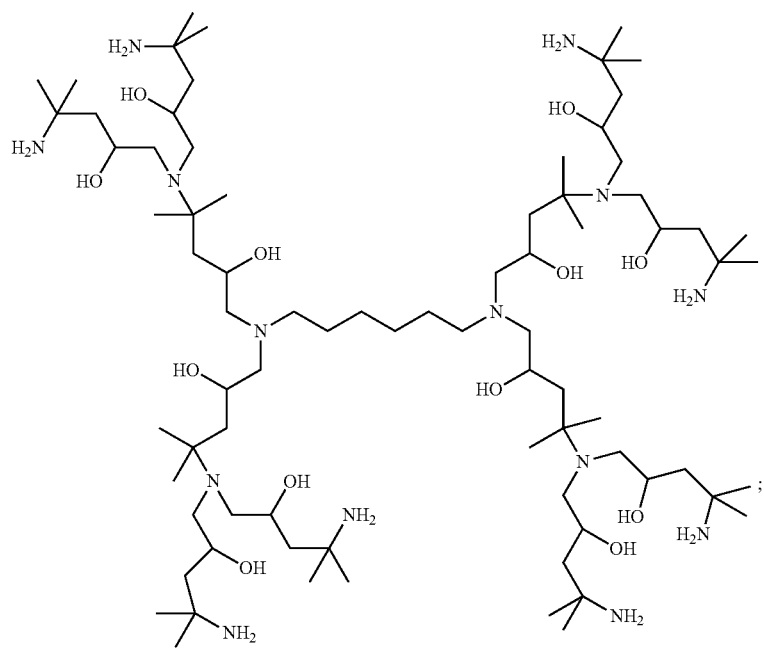
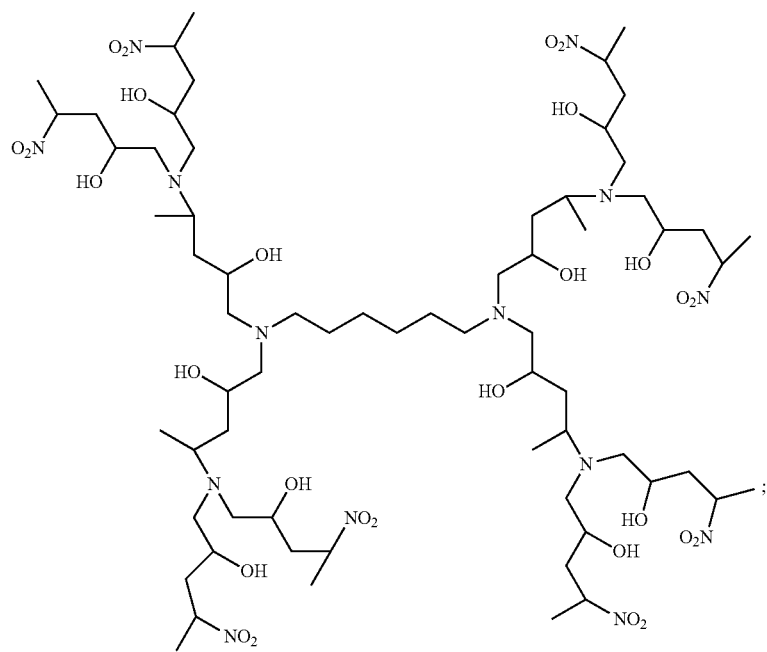

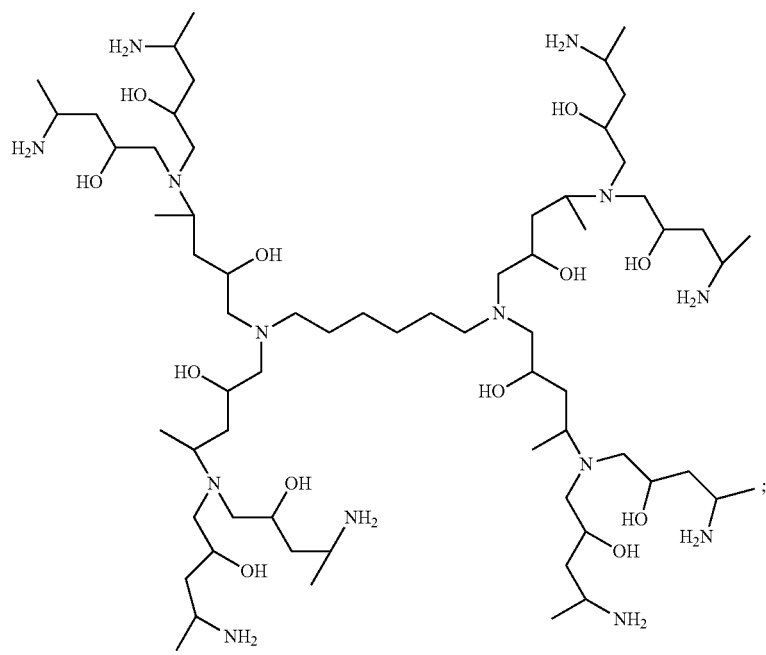
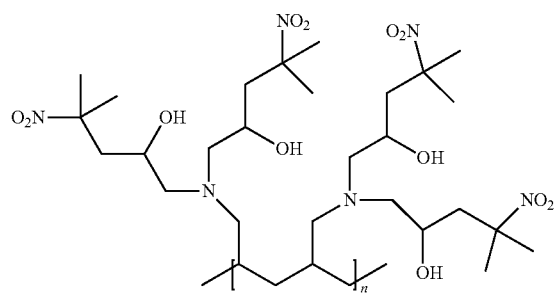
wherein n is 100 to 1500;
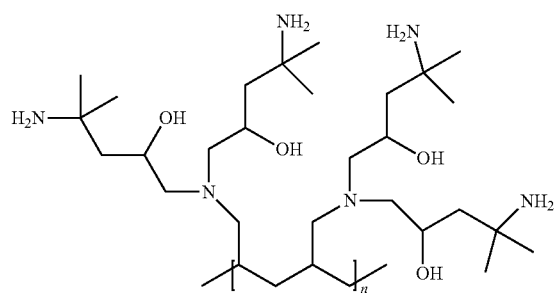
wherein n is 100 to 1500;

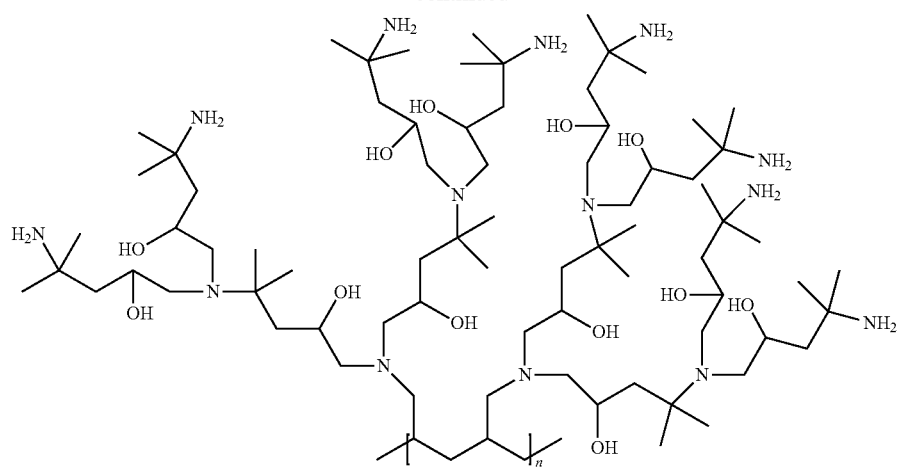
wherein n is 100 to 1500;
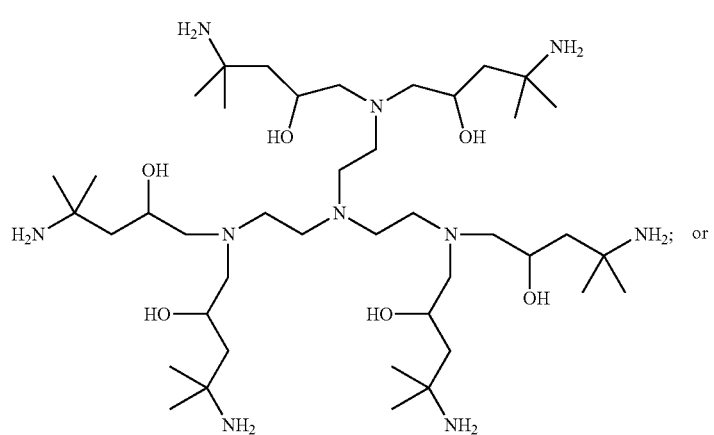 or
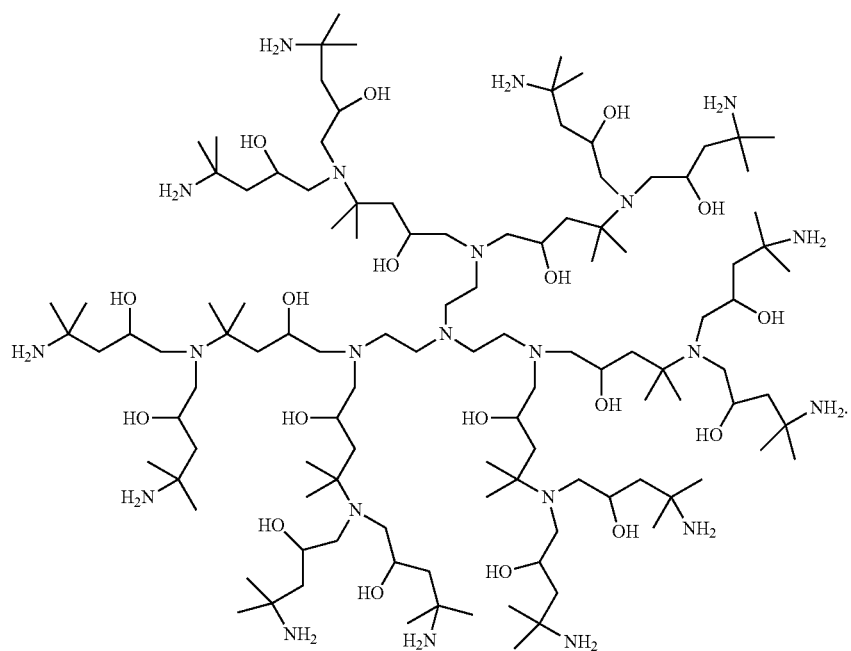

6. A process for making a dendrimer comprising:
a core comprising 2 or more terminal residues and derived from a polyvalent organic molecule;
from 1 to 8 generations emanating radially from the core, the 1 to 8 generations comprising:
from 0 to 7 interior generations comprising 2 or more molecular units independently having formula A:

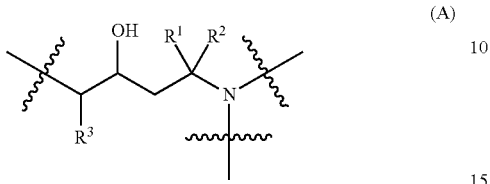

wherein $R^1$ and $R^2$ are independently H or $C_1$-$C_{10}$ alkyl, or $R^1$ and $R^2$, together with the carbon to which they are attached, form a $C_3$-$C_{12}$ cycloalkyl ring optionally substituted with $C_1$-$C_6$ alkyl, and $R^3$ is H, $C_1$-$C_{10}$ alkyl, or phenyl, and wherein the innermost interior generation is attached to the core through the terminal residues;
an exterior layer attached to the outermost of the interior generations or to the core through the terminal residues if no interior generations are present, the exterior layer comprising 2 or more molecular units independently having formula B:

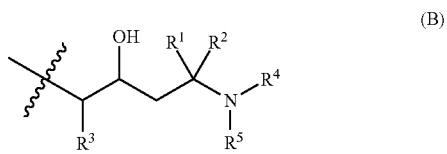

wherein $R^4$ and $R^5$ are each H, or $R^4$, $R^5$ and the nitrogen to which they are attached form a $NO_2$ group,
wherein the terminal residues are amine residues, the process comprising:
(a) providing a polyvalent organic molecule comprising 2 or more terminal functional groups;
(b) combining a nitroalkyloxirane compound of formula III:

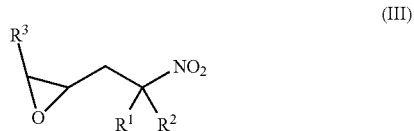

with the polyvalent organic molecule in sufficient amount such that the nitroalkyloxirane compound reacts with the terminal functional groups of the polyvalent organic molecule to form a nitro compound comprising a core and 2 or more molecular units connected to the core and independently having formula B-1:

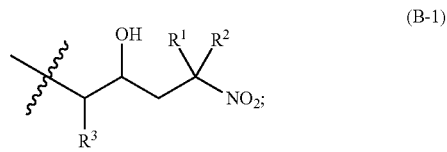

(c) optionally reducing the nitro compound to form an amine compound comprising the core and 2 or more molecular units connected to the core and independently having formula B-2:

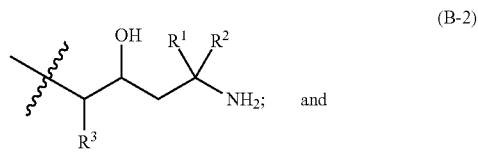

(d) optionally repeating steps (b) and/or (c) from 1 to 7 times, wherein the amine compound instead of the polyvalent organic molecule is reacted with a nitroalkyloxirane compound of formula III,
wherein the terminal functional groups of the polyvalent organic molecule are amines.

7. The process of claim 6 wherein $R^4$, $R^5$ and the nitrogen to which they are attached form a $NO_2$ group, and the dendrimer is further functionalized to form a functionalized dendrimer by: base catalyzed reaction with an aldehyde (Henry Reaction); base catalyzed reaction with an α,β-unsaturated ester or nitrile (Michael Reaction); base catalyzed reaction with an aldehyde in the presence of an amine (Mannich Reaction); strong base catalyzed reaction with an alkyl halide (alkylation); strong base catalyzed reaction with an acyl chloride or activated ester (acylation); or base catalyzed halogenation.

8. The process of claim 6 wherein $R^4$ and $R^5$ are H, and the dendrimer is further functionalized to form a functionalized dendrimer by reaction with an epoxide, acrylate, or acid chloride.

9. The process of claim 7 wherein the dendrimer is further functionalized with a dye, a drug, or a drug targeting molecule.

10. The process of claim 8 wherein the functionalized dendrimer is of the structure:

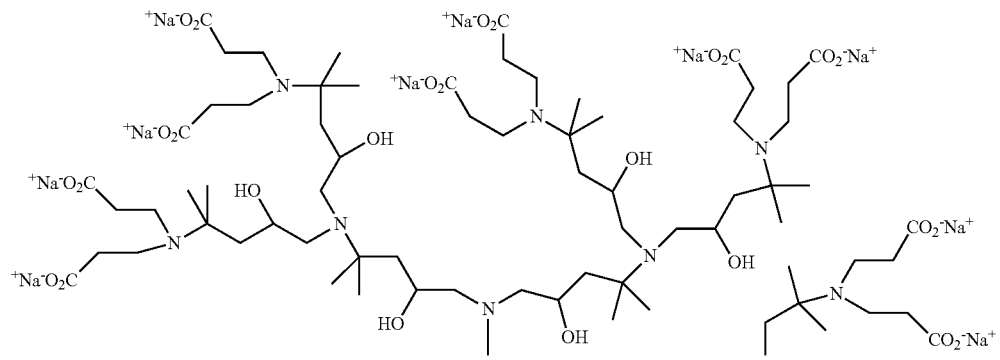

-continued
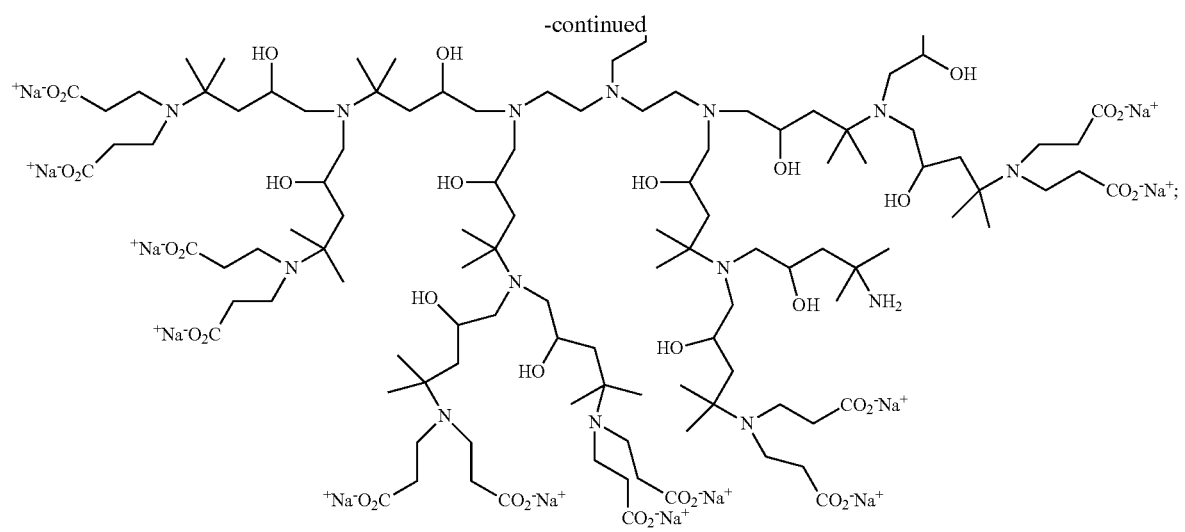
or
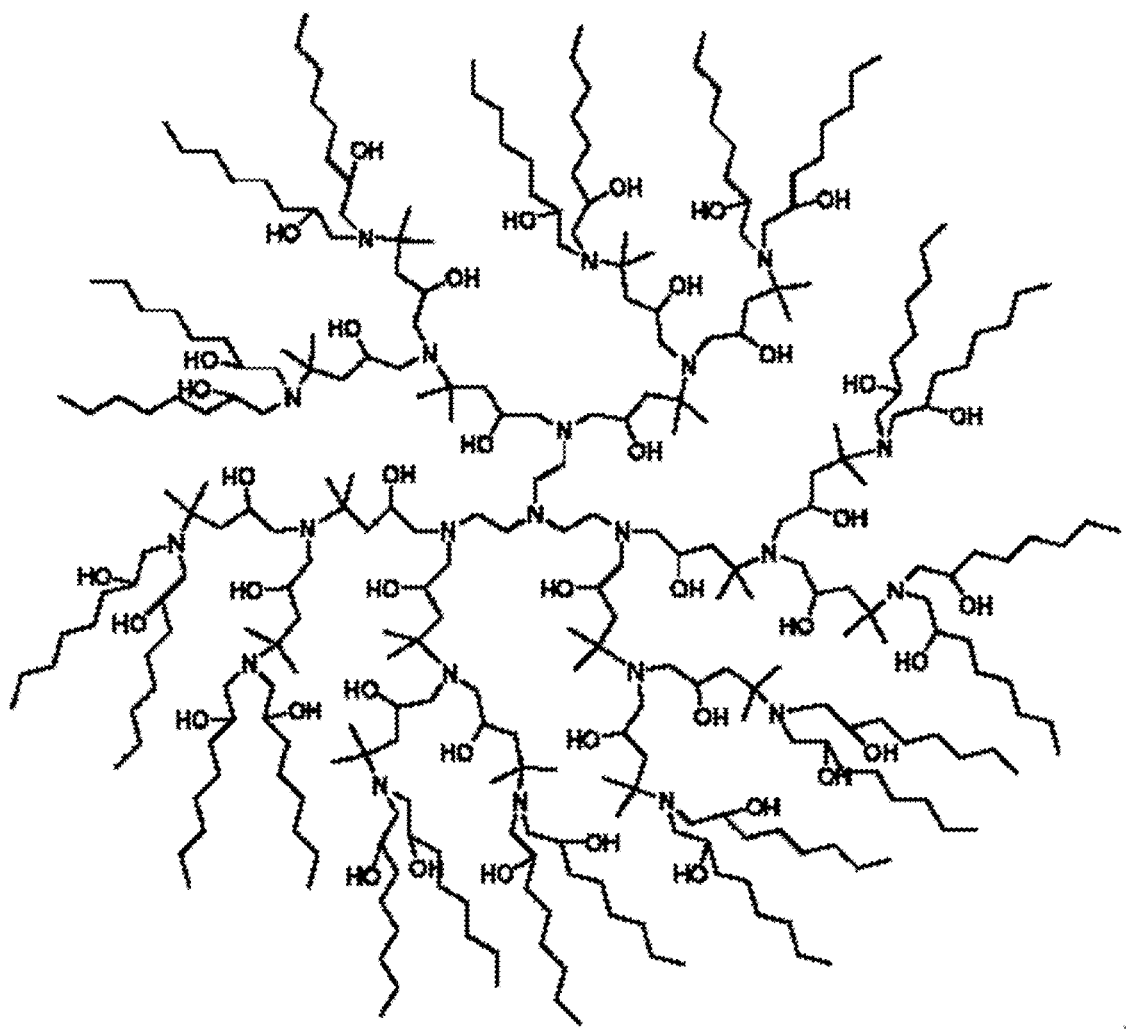
* * * * *